United States Patent
Levin (10) Patent No.: US 8,986,985 B2
(45) Date of Patent: Mar. 24, 2015

(54) PHOTOBIOREACTOR

(71) Applicant: Alexander Levin, Binyamina (IL)

(72) Inventor: Alexander Levin, Binyamina (IL)

(*) Notice: Subject to any disclaimer, the term of this patent is extended or adjusted under 35 U.S.C. 154(b) by 225 days.

(21) Appl. No.: 13/633,912

(22) Filed: Oct. 3, 2012

(65) Prior Publication Data
US 2014/0093950 A1    Apr. 3, 2014

(51) Int. Cl.
*C12M 3/00*    (2006.01)
*C12M 1/00*    (2006.01)

(52) U.S. Cl.
CPC ............... *C12M 21/02* (2013.01); *C12M 23/20* (2013.01); *C12M 23/22* (2013.01); *C12M 23/38* (2013.01)
USPC ................... 435/292.1; 435/289.1; 435/294.1; 435/305.1; 435/305.2; 435/305.3

(58) Field of Classification Search
CPC ...... C12M 21/02; C12M 31/02; C12M 31/10; C12M 31/00; C12M 23/22; C12M 23/48
USPC .......... 435/292.1, 289.1, 294.1, 305.1, 305.2, 435/305.3
See application file for complete search history.

(56) References Cited

U.S. PATENT DOCUMENTS

| | | | |
|---|---|---|---|
| 2007/0155006 A1* | 7/2007 | Levin | 435/292.1 |
| 2012/0129243 A1* | 5/2012 | Cloud et al. | 435/257.1 |
| 2012/0315692 A1* | 12/2012 | Hu et al. | 435/292.1 |
| 2013/0042522 A1* | 2/2013 | Delobel | 47/1.4 |
| 2013/0109084 A1* | 5/2013 | Woods et al. | 435/292.1 |
| 2013/0205450 A1* | 8/2013 | Lu et al. | 800/298 |
| 2013/0224853 A1* | 8/2013 | van Walsem et al. | 435/292.1 |

* cited by examiner

*Primary Examiner* — Nathan Bowers (57) ABSTRACT

An invention proposes a photobioreactor with a cultivation chamber in the form of a shallow closed trough that is irradiated by the sun light. The bottom section of the shallow closed trough comprises an elongated polymer flexible film, which is arranged with small inclination to the horizontal plane; the middle longitudinal section of the elongated polymer flexible film plays a role of the bottom cover of the shallow closed trough. A bank of translucent or transparent flat rigid members, which are abutted in-line with a small inclination to the horizontal plane, provides required rigidity to the entire photobioreactor. The translucent or transparent flat rigid members are provided with longitudinal bottom spacers and joined with the lateral longitudinal sections of the elongated polymer flexible film. In addition, the translucent flat rigid members serve for closing the shallow trough from above.

22 Claims, 11 Drawing Sheets

PHOTOBIOREACTOR

BACKGROUND OF THE INVENTION

This invention relates to the field of bioreactors for cultivation of microalgae or cyanobacteria.

Mass cultivation of microalgae or cyanobacteria has a great potential for modern agriculture, biochemistry and pharmaceutics.

Algal species: *Spirulina, Dunaliella* and others present important sources of vitamins, proteins, unsaturated fats, organic compounds of iron and other microelements. The most common forms of microalgae or cyanobacteria cultivation photobioreactors are open ponds or open raceways channels.

There are some technical problems connected with application of such systems:

a) Light distribution within photobioreactors constructed as ponds or channels presents a serious problem. The depth of the pond or raceway channels should be in the range of 15/30 cm.

It determines in turn relatively low final microalgae (or cyanobacteria) concentration in nutritious solution and high cost of harvesting microalgae biomass.

b) Mixing the nutritious solution in order to prevent cell sinking, and, in addition, to remove from the nutritious solution the generated oxygen, which inhibits photosynthesis process.

c) It is necessary to provide an adequate amount of $CO_2$, which is required for performance of photosynthesis process; this $CO_2$ is supplied as a rule from the ambient air or from gaseous medium enriched with $CO_2$ by its dissolution in the nutritious solution.

d) Maintenance of optimum ranges of daily and nightly temperatures of the nutritious solutions.

There are patents and patent applications, which are devoted to solve a part of the above-mentioned problems; however, these patents and patent applications do not provide sufficiently effective and cheap solutions of the described problems.

U.S. Pat. No. 4,084,346 describes a system of channels intended for algae growing; there are discharge means installed in these channels which introduce $CO_2$, into the microalgae suspension.

U.S. Pat. No. 3,468,057 describes a basin for culture of algae in an aqueous nutrient medium comprising, in combination, at least two illuminated horizontal zones, at least two inclined zones and at least one gas injection means.

U.S. Pat. No. 3,955,317 describes a method for growing plant cells containing chloroplasts in liquid suspension simultaneously with the growth of photosynthetic bacteria, in which method the liquid suspension containing the plant cells is enclosed in a first elongated, at least partially transparent, container and a liquid suspension of photosynthetic bacteria is contained in second elongated, at least partially transparent, container, the said second container being attached to the said first container so that light passing through the said first container then passes through the said second container; the said containers preventing passage of liquid from one container to the other, the containers being supported on a body of water; the liquid suspension in the first container being exposed to light and brought into contact with carbon dioxide.

U.S. Pat. No. 3,998,186 describes a method and apparatus for shrimp culture; shrimp hatched and brought through larval and post-larval stages environment unit which includes plastic cover means positioned over an elongated waterway containing seawater, or the like, and algae in substantial amounts. The design of the unit and the technique of intermittently supplying seawater allows the control of light intensity and light spectral characteristics within the shrimp growing area and the control of seawater flow rate, temperature and dissolved oxygen content of the seawater in the waterway.

U.S. Pat. No. 5,443,985 describes a bioreactor for culturing living cells, particularly shear sensitive cells, wherein the bioreactor is composed of a stationary vessel with opposite spaced walls inclined at an angle to form upper and lower walls. Liquid culture medium and cell culture, such as hybridoma cells, are introduced into the vessel and gas is introduced at the lower end of the vessel to form gas bubbles which travel upward along the upper wall of the bioreactor to disengage from a small portion of the gas liquid interface. The gas bubbles circulate the cells and liquid medium, maintaining the cells in suspension and lifting them in a circulating path upwardly parallel to the upper wall and downward along the lower wall. The bioreactor design thus achieves bulk mixing and aeration by maintaining a significant degree of segregation between the upwardly travelling bubbles and the cells in the liquid medium avoiding unnecessary cell damage by fluid-mechanical shear or by bubble bursting events.

U.S. Pat. No. 5,534,417 describes a method of growing microalgae, which uses the outdoor sunlight as a source of energy. Growth is confined to an assembly of vertical, transparent tubes through which nutrient and air is carried with carbon dioxide. The microalgae is periodically harvested from the tubes.

U.S. Pat. No. 5,741,702 describes a reactor vessel for processing gases containing carbon dioxide by means of a fluid containing algae; this reactor vessel comprises: a first elongated duct having a rectangular cross section with a top surface and a bottom surface for containing said gases and said fluid containing algae; a second elongated duct, abutting said first elongated duct, having a rectangular cross section with a top surface and a bottom surface, said duct having ribs extending from said bottom surface to said top surface to form a plurality of elongated channels for insulating said first elongated duct; wherein the channels of said second elongated duct are constructed so as to be evacuated to create a vacuum therein.

U.S. Pat. No. 5,846,816 describes a bioreactor for biomass production comprising: a substantially transparent chamber, the chamber being at least suitable for containing biomass in a liquid phase, and having a base portion, an upper portion and a number of side walls between the base portion and the upper portion, the side walls being configured so as to generally diverge from the base portion towards the wider upper portion; and circulating means for circulating the contents of the chamber, wherein the circulating means creates a motive force within the liquid phase sufficient to ensure continual mixing of substantially all of the biomass and at least cyclical exposure of biomass to a light source.

U.S. Pat. No. 5,981,271 describes process of outdoor thin-layer cultivation of algae in which suspension of algae saturated with carbon dioxide and enriched with necessary nutrients, is distributed on inclined cultivation areas where the suspension of algae is distributed on inclined cultivation areas under turbulent flow which depends on velocity of flow, on coefficient of roughness of the cultivation surfaces, on the thickness of the algal suspension layer and on inclination of the cultivation surface. Between individual cultivation areas carbon dioxide is supplied into the suspension and the suspension flowing from the lowest cultivation area is conveyed into the collecting tank from which it is pumped on the upper edge of the highest cultivation area. Bioreactor for accomplishing the mentioned process is composed of at least two individual cultivation meandering areas where the lower end of the upper area and the beginning of the next lower area, inclined in the opposite direction, are connected by channels in which outlets for supply of carbon dioxide into suspension are placed.

U.S. Pat. No. 8,110,395 describes a photobioreactor system comprising: a plurality of interconnectable photobioreactor sections which, when connected together, form at least one longitudinally-oriented photobioreactor unit of the photobioreactor system, the photobioreactor sections each comprising a liquid flow channel, and a light-transparent cover that forms a gas headspace between the cover and the liquid flow channel, the cover being constructed and arranged to cover at least a substantial portion of the liquid flow channel and configured to provide the gas headspace even when a gas pressure within the photobioreactor unit is less than the atmospheric pressure surrounding the photobioreactor section, at least one photobioreactor unit of the photobioreactor system further including an evaporative cooling area, including a reservoir and a sprayer, the evaporative cooling area being disposed outside of the cover such that the reservoir is open to the atmosphere outside of the cover, the reservoir being in fluid communication with the liquid flow channel, the sprayer is configured to spray a liquid upwardly from within the reservoir.

U.S. Pat. No. 6,827,036 describes aquaculture apparatus comprising an elongate tube of flexible translucent material, the tube extending longitudinally along a tube site and having a lower section defining a water course, and a cover extending externally over the tube and being air supported, said cover being at least partially spaced from the tube and providing an insulating space for insulating at least a substantial part of the tube.

U.S. Patent Application No. 20090130706 describes an enclosed photobioreactor configured to float on a body of water; the photobioreactor comprises: an elongated, longitudinally-oriented photobioreactor section constructed and arranged to contain a liquid medium comprising phototrophic organisms therein, the photobioreactor section comprises: a substantially flexible lower barrier comprising an upper surface in contact with and supporting the liquid medium; a cover constructed and arranged to cover the liquid medium within the photobioreactor section and further constructed and arranged to provide a gas headspace under the cover and above the liquid medium, the cover being at least partially transparent to light of a wavelength capable of driving photosynthesis; a first floatation element disposed on a first lateral side of the photobioreactor section; a second floatation element disposed on a second lateral side of the photobioreactor section; the first and second floatation elements being constructed and arranged to support the photobioreactor section for floatation on the body of water; and a plurality of tensioners constructed and arranged to apply tension to the lower barrier so as to maintain a substantial portion of the area of the lower barrier in a substantially horizontal configuration when the photobioreactor section is charged with the liquid medium, such that a continuous layer of the liquid medium has a substantially uniform depth which extends from approximately the first floatation element to approximately the second floatation element over at least a portion of the area of the lower barrier.

U.S. Patent Application No. 20100028976 describes a photobioreactor comprising: (a) a container adapted for holding fluid, comprising (i) opposing first and second sidewalls, wherein at least one of the first and second sidewalls is transparent; (ii) opposing first and second endwalls; (iii) a container bottom; and (iv) a container cover, wherein the first and second sidewalls comprise a plurality of separate sections, and wherein the separate sections are in fluid communication; (b) support struts for connecting the plurality of separate sections of the first and second sidewalls; (c) at least one inlet port in fluid communication with the container; (d) at least one outlet port in fluid communication with the container; (e) an aeration system in fluid communication with the container; and (f) a temperature control system connected to the container so as to control temperature of fluid within the container.

Reviews of technical problems connected with design of industrial photobioreactors are presented in the articles: James C. Ogbonna, Hideo Tanaka "Industrial-size photobioreactors" CHEMTECH 1997, 27(7), 43-49. and O. Pulz "PHOTOBIOREACTORS: PRODUCTION SYSTEM FOR PHOTOTROPHIC MICROORGANISMS" Springer-Verlag, 2001.

It should be noted that these US Patents and Patent Applications (including U.S. Pat. No. 5,981,271) do not solve construction problems of an elongated photobioreactor with length of some tens of meters to some hundreds of meters and with small inclination regarding the horizontal plane, wherein such photobioreactor is provided with effective means for enhancement of heat and mass transfer between the liquid and gaseous mediums in it.

SUMMARY OF THE INVENTION

An invention proposes a photobioreactor with a microalgae (or cyanobacteria) photo-cultivation chamber constructed as a shallow closed trough, which is irradiated by the sun light. The bottom section of the shallow closed trough is constructed from an elongated polymer flexible film, which is arranged with a small inclination to the horizontal plane and the middle longitudinal section of this elongated polymer flexible film fulfils a role of the bottom cover of the shallow closed trough.

There are two parallel posts' rows and two parallel rows of inclined supporting angles, which are installed on these posts. These posts and supporting angles form a supporting structure with the preset inclination angle, preferably, in the range of 0.1 degree÷2. degree and this supporting structure serves for installation of a bank of translucent (or transparent) flat rigid members in combination with abovementioned elongated polymer flexible film; the translucent flat rigid members are abutted in-line with the small inclination to the horizontal plane.

The translucent flat rigid members are provided with longitudinal spacers on their undersides and joined with the lateral longitudinal sections of the elongated polymer flexible film. In addition, the translucent flat rigid members serve for closing the obtained shallow trough from above.

In such a way, the shallow closed trough has a suspended bottom cover from the elongated polymer flexible film.

The terminal sections of the shallow closed trough are provided with inlet and outlet ports in the case of gas-liquid co-current flow in the shallow closed trough, or with inlet-outlet ports in the case of gas-liquid counter flow in the shallow closed trough.

In addition, there is an array of transverse channel bars joined with the abovementioned supporting angles on their undersides; these transverse channel bars serve for insertion for a while auxiliary flat supporting members during spreading the elongated flexible polymer film in the process of assembling the shallow closed trough.

It is possible to fabricate the supporting angles from ferromagnetic steel; in this case the auxiliary supporting members for spreading the flexible polymer film may be constructed as auxiliary flat supporting members with magnets installed on their longitudinal edges; in such a way, these magnets serve for fastening for a while these auxiliary flat supporting members from under the supporting angles without application of the transverse channel bars.

It should be noted that the angles of inclination of the supporting angles may be of variable values.

In particular, these angles of inclination may be of relatively small values for the proximal sections of the shallow closed trough (regarding flow direction of the microalgae suspension) with gradually increasing the inclination angles at the middle and distal sections of the shallow closed trough. It allows to choose an optimal change of the microalgae suspension depth along the whole length of the shallow closed trough.

The width of the elongated flexible polymer film is in excess of the distance between the parallel rows of the supporting angles.

At a specific stage of assembling the shallow closed trough, the translucent flat rigid members are positioned above the spread flexible polymer film with supporting by the above-mentioned supporting angles; then the both longitudinal lateral sections of the flexible polymer film are bent round the edges of the translucent flat rigid members. Thereafter the both longitudinal lateral sections of the flexible polymer film are locked with the flat longitudinal zones on the upper surfaces of the flat translucent flat rigid members.

The translucent flat rigid members can be realized as glass panes provided on their underside surfaces with longitudinal spacers, which are glued to these surfaces. The edges of the glass panes are preferably ground.

These longitudinal spacers are fabricated preferably from ferromagnetic stainless steel.

Locking the both longitudinal lateral sections of the flexible polymer film with the glass panes can be executed by gluing. The upper surface of the longitudinal lateral sections of the flexible polymer film can be treated for this aim by known methods imparting hydrophilic property to the surfaces of these longitudinal sections.

In addition, a sealing putty can be applied for locking sealingly the elongated flexible polymer film with the glass panes. The places of application of the sealing putty (including the places of the butt joints between the adjacent glass panes) can be covered by pieces of glass panes, which overlap these places.

In such a way, this sealing putty in combination with the pieces of the glass panes overlapping the butt joints and the both longitudinal lateral sections of the flexible polymer film provides a required degree of sealing the internal space of the shallow closed trough. The pieces of the glass panes and/or the glass panes can be produced from UV absorbing glass.

The longitudinal lateral sections of the flexible polymer film with the glass panes and the pieces of the glass panes can be forced against the supporting angles by screw clamps.

In another version, the butt joints between the adjacent translucent flat rigid members and the both longitudinal lateral sections of the flexible polymer film are sealed by a sealing tape, which overlaps these butt joints and the edges of the both longitudinal lateral sections of the flexible polymer film.

In addition, it is possible to apply rigid Perspex sheets instead of the glass panes. In this case, both longitudinal lateral sections of the flexible polymer film can be immediately joined with these rigid Perspex sheets by plastic welding.

In another version, the translucent flat rigid members are designed as perforated plates (for example, from stainless steel) provided with longitudinal spacers on their underside and longitudinal zones with certain widths.

In this case, these longitudinal zones serve as auxiliary supporting means for welding the both longitudinal lateral sections of the flexible polymer film with another elongated flexible polymer film, which overlaps these longitudinal lateral sections of the elongated flexible polymer film.

In an additional version, the longitudinal lateral sections of the flexible polymer film are overlapped and joined longitudinally by plastic welding with forcing against the longitudinal zones of the perforated plates.

This technical solution can be used as well in the case of application of the glass panes as the translucent flat rigid members.

The translucent flat rigid members can be designed as grates with longitudinal zones serving for welding the longitudinal lateral sections of the elongated flexible polymer film as it has been described above.

The perforated plate or the grate can be fabricated from a translucent or transparent material.

In a further version the translucent flat rigid member is constructed as a flat W shaped unit (according to the terms of Hot Rolled Shapes) with two flanges and a web; this flanges are provided with longitudinal spacers fastened on their undersides and with two elongated pane pieces, which are installed on the ends of the flat W shaped unit.

It should be noted that such longitudinal pane pieces can be installed on the longitudinal edges of the perforated plate or grate described above.

For all cases described above, the terminal flat rigid members serve only as supporting means for welding the both longitudinal lateral sections of the flexible polymer film with polymer film sheets, which overlap the both longitudinal lateral sections of the elongated flexible polymer film. In such a way, these terminal sections of the shallow closed trough are shaped as two sleeves.

Thereafter, these terminal flat rigid members should be removed, and inlet and outlet ports (regarding flow direction of the liquid medium) are formed in these sleeves by welding operation, which is executed between the elongated flexible polymer film and the polymer film sheets with application of auxiliary supporting flat plates. These auxiliary supporting flat plates are positioned from aloft the terminal sleeves and should be removed after formation the inlet and outlet ports in the terminal sleeves.

The inlet and outlet ports are in fluid communication with two headers, which serve for supply of the air or gaseous medium enriched with $CO_2$ into the internal space of the shallow closed trough and removal of the air or the gaseous medium from this internal space. In addition, these ports serve for supply of suspension of microalgae or cyanobacteria into internal space of the shallow closed trough and withdrawal of suspension of microalgae or cyanobacteria from this internal space.

Air or gaseous medium supplied into the proximal header (regarding flow direction of the gaseous medium) can be previously cooled and/or dried; it allows to establish optimal temperature of the microalgae suspension along the shallow closed trough.

In order to decrease deflection downwards of the middle longitudinal section of the elongated flexible polymer film, which forms the suspended bottom cover of the shallow closed trough, it is possible to apply a bank of magnets, which force at the bottom of the elongated flexible polymer film against the longitudinal spacers of the translucent flat rigid members. In this case the longitudinal spacers are fabricated from ferromagnetic material.

It should be noted, that the elongated flexible polymer film, which fulfils a role of the bottom cover of the shallow closed trough, is functioning as a flexible elastic membrane. Such flexible membrane vibrates in response to the gaseous medium flow with enhancement of heat and mass transfer between the gaseous medium and the thin layer of microalgae suspension.

Application of this effect in heat exchangers is described in the article: Yanhua Lu et al. ENHANCED PERFORMANCE OF HEAT RECOVERY BY AIR-INDUCED FILM VIBRATION, International Journal of Thermal Science, 49, July 2010 pp. 2037/2041.

This effect can be enhanced by variable pressure in the internal space of the shallow closed trough, when this pressure variation is executed with a specific frequency.

The elongated flexible polymer film can be transparent or translucent polymer film. This allows to utilize solar radiation reflected from below onto the shallow closed trough.

There is another method of setting off vibration of the bottom cover of the shallow closed trough.

This effect can be obtained by application of intermittent air jets, which are arrive onto the underside of the bottom cover from a flat zigzag pipe with a set of perforations oriented toward the bottom cover; pressurized air with pulsating pressure is supplied into this flat zigzag pipe.

The proximal section (regarding a flow direction of the microalgae suspension) of the supporting angles can be provided with aligning screws in order to minimize misalignment of the proximal supporting member and to achieve even distribution of the microalgae suspension across the width of the shallow closed trough.

In addition, other sections of the supporting angles may be provided with such aligning screws.

BRIEF DESCRIPTION OF THE DRAWINGS

In this case the photobioreactor operates with counter-flow of microalgae suspension and gaseous medium containing CO.sub.2.

DESCRIPTION OF PREFERABLE EMBODIMENTS

Figure 1:
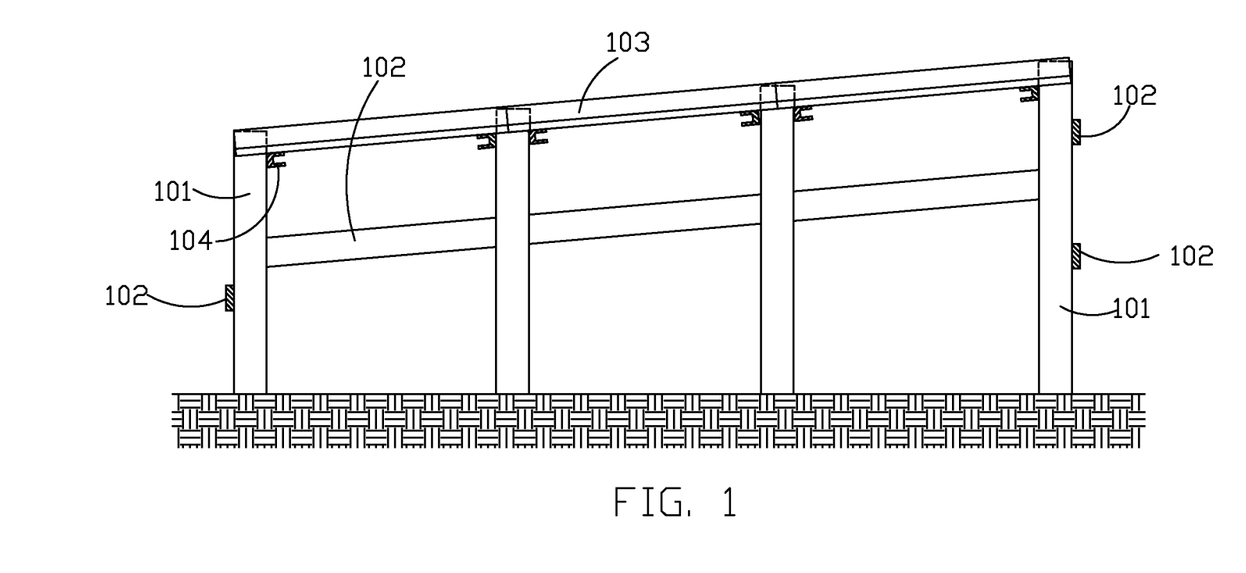
FIG. 1 demonstrates a side view of supporting angles installed on posts.

FIG. 1 demonstrates a side view of supporting angles installed on posts. It comprises: posts 101 with cross-bars 102; a supporting angle 103 and transverse channel bars 104.

Figure 2A:
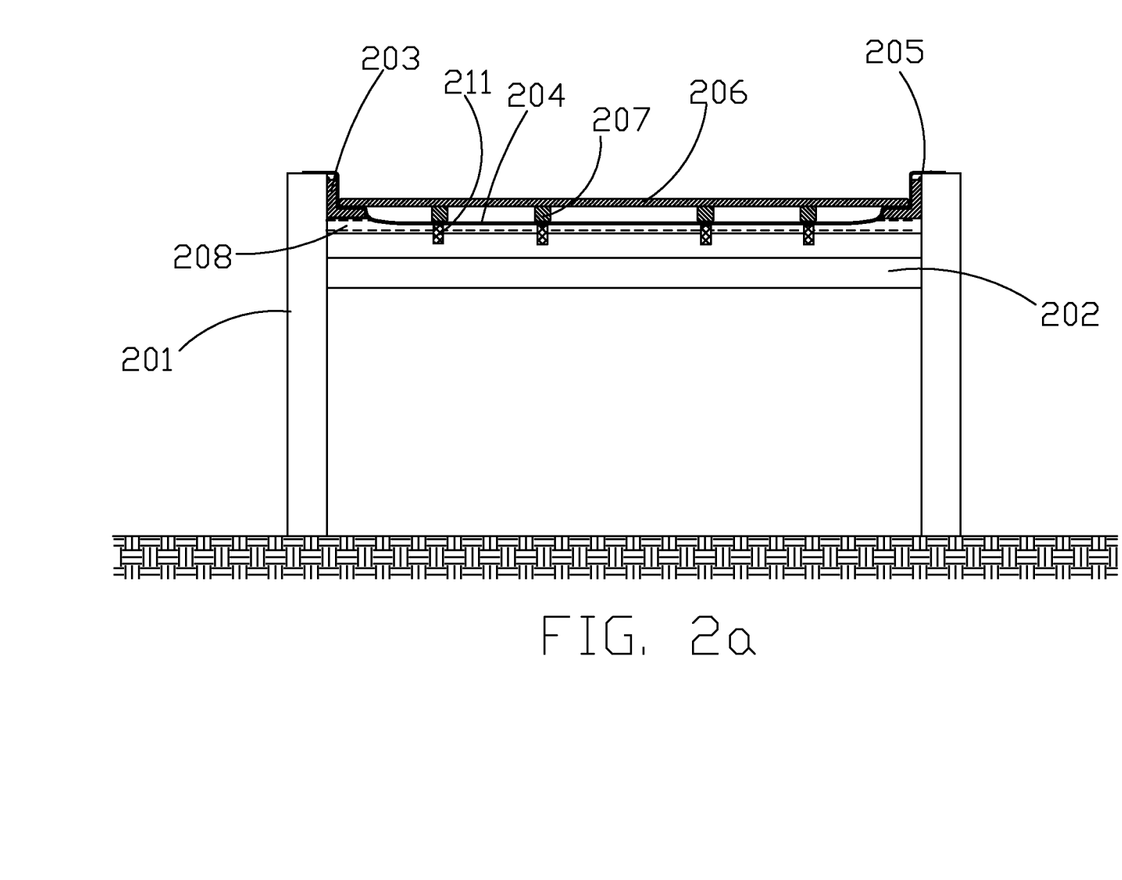
FIG. 2a shows a cross-section of a shallow closed trough arranged on the supporting angles in a stage, which comes before bending both longitudinal lateral sections of a flexible polymer film around the longitudinal edges glass panes.

FIG. 2a shows a cross-section of a shallow closed trough arranged on the supporting angles in a stage, which comes before bending both longitudinal lateral sections of a flexible polymer film around longitudinal edges of a glass pane fulfilling a role of the flat rigid member.

It comprises: posts 201; cross-bar 202, supporting angles 203 installed on posts 201; a flexible polymer film 204 with longitudinal lateral sections 205; a glass pane 206 with longitudinal spacers 207, which are fabricated from a ferromagnetic material and attached on the underside of the glass pane 206; a transverse channel bar 208, which is installed on the underside of the supporting angles 203 and serves for insertion for a while an auxiliary flat supporting member.

Figure 2B:
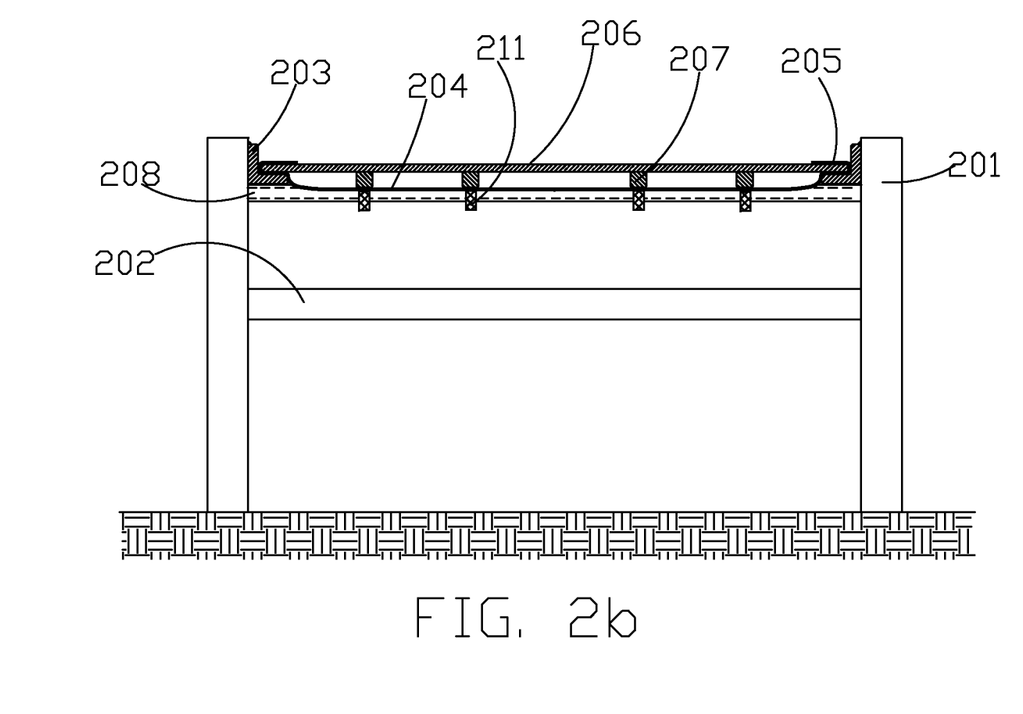
FIG. 2b shows the cross-section of the shallow closed trough arranged on the supporting angles upon bending both longitudinal lateral sections of the flexible polymer film around the longitudinal edges of the glass panes with their following adjacency to the glass panes.

FIG. 2b shows the cross-section of the shallow closed trough arranged on the supporting angles upon bending both longitudinal lateral sections of the flexible polymer film around the longitudinal edges of the glass pane with their following adjacency to the glass pane.

It comprises: posts 201; cross-bar 202; the supporting angles 203 installed on posts 201; the elongated flexible polymer film 204 with the longitudinal lateral sections 205; the glass pane 206 with longitudinal spacers 207, which are fabricated from the ferromagnetic material and attached on the underside of the glass pane 206; the transverse channel bar 208, which is installed on the underside of the supporting angles 203 and serves for insertion for a while the auxiliary flat supporting member; the longitudinal lateral sections 205 are glued to the glass pane 206.

Figure 2C:
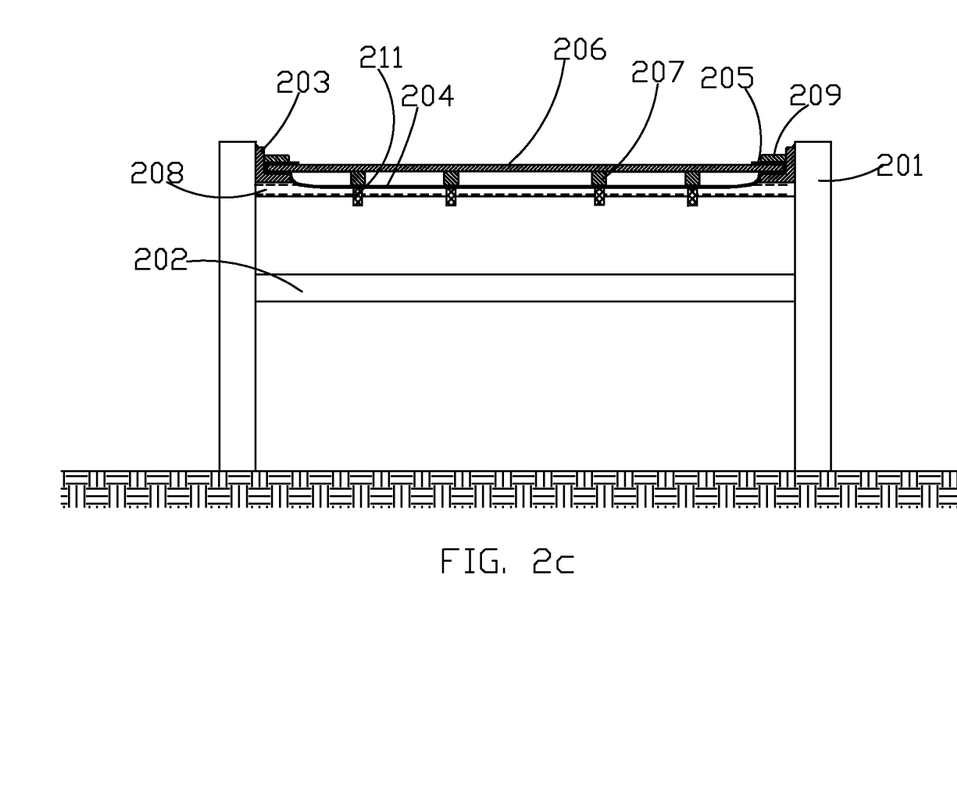
FIG. 2c shows the cross-section of the shallow closed trough arranged on the supporting angles upon bending both longitudinal lateral sections of the flexible polymer film around the longitudinal edges of the glass panes with their following adjacency to the glass panes and forcing the both longitudinal lateral sections of the flexible polymer film against the glass panes by glass pane pieces.

FIG. 2c shows the cross-section of the shallow closed trough arranged on the supporting angles upon bending both longitudinal lateral sections of the elongated flexible polymer film around the longitudinal edges of the glass pane with their following adjacency to the glass pane and forcing the both longitudinal lateral sections of the elongated flexible polymer film against the glass pane by glass pane pieces.

It comprises: posts 201; cross-bar 202; the supporting angles 203 installed on posts 201; the elongated flexible polymer film 204 with the longitudinal lateral sections 205; the glass pane 206 with the longitudinal spacers 207, which are fabricated from the ferromagnetic material and attached on the underside of the glass pane 206; the transverse channel bar 208, which is installed on the underside of the supporting angles 203 and serves for insertion for a while the auxiliary flat supporting member; the both longitudinal lateral sections 205 of the elongated flexible polymer film 204 are forced against the glass pane 206 by glass pane pieces 209.

Figure 2D:
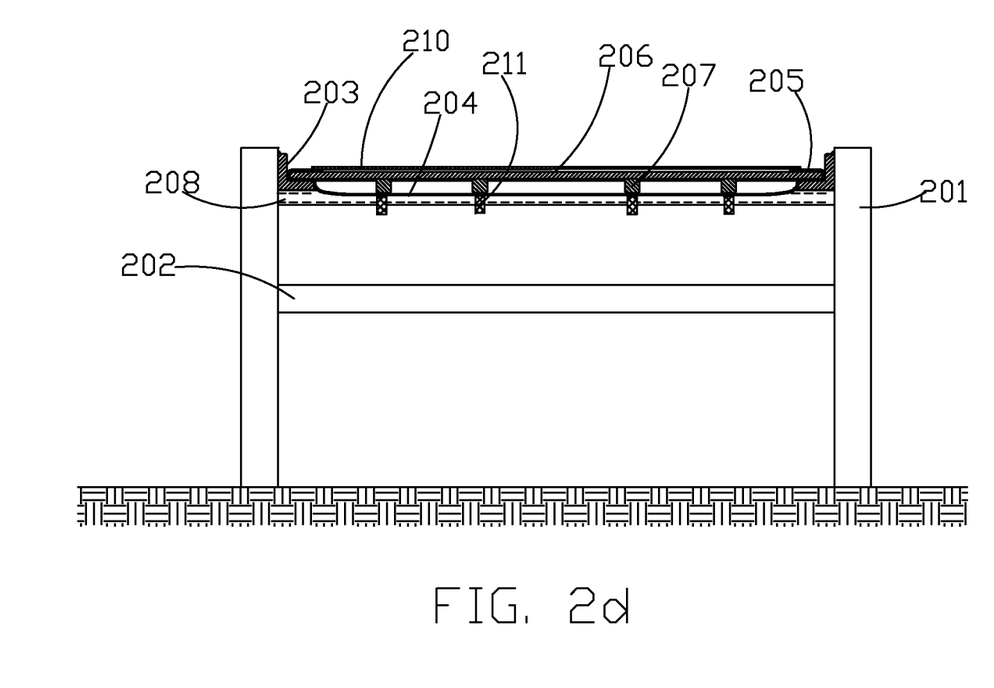
FIG. 2d shows the cross-section of the shallow closed trough arranged on the supporting angles upon bending both longitudinal lateral sections of the flexible polymer film around the longitudinal edges of the glass panes with their following adjacency to the glass panes and welding these longitudinal lateral sections of the elongated flexible polymer film with an additional elongated flexible polymer film, which overlaps the longitudinal lateral sections of the elongated flexible polymer film.

FIG. 2d shows the cross-section of the shallow closed trough arranged on the supporting angles upon bending both longitudinal lateral sections of the elongated flexible polymer film around the longitudinal edges of the glass pane with their following adjacency to the glass pane and welding these longitudinal lateral sections of the elongated flexible polymer film with an additional elongated flexible polymer film, which overlaps these longitudinal lateral sections of the elongated flexible polymer film.

It comprises: posts 201; cross-bar 202, the supporting angles 203 installed on posts 201; the elongated flexible polymer film 204 with the longitudinal lateral sections 205; the glass pane 206 with the longitudinal spacers 207, which are fabricated from the ferromagnetic material and attached on the underside of the glass pane 206; the transverse channel bar 208, which is installed on the underside of the supporting angles 203 and serves for insertion for a while the auxiliary supporting member; an additional elongated flexible polymer film 210, which overlaps the longitudinal lateral sections 205 of the elongated flexible polymer film 205 and is joined with them by plastic welding.

Figure 3A:
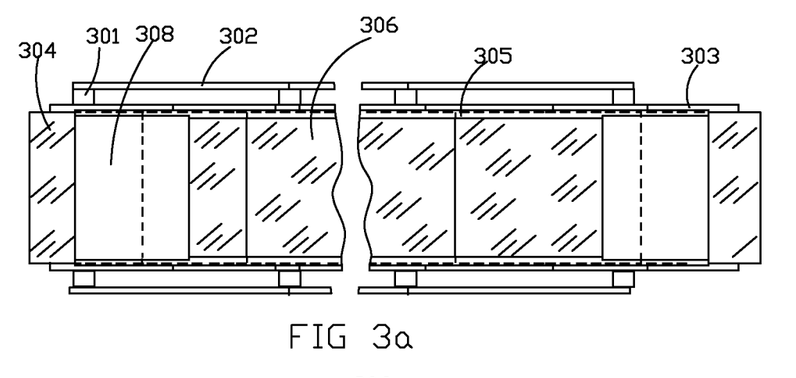
FIG. 3a shows a top view of a shallow closed trough in a preliminary stage of its assembling with a bank of glass panes including auxiliary terminal flat rigid members.

FIG. 3a shows a top view of the shallow closed trough in a preliminary stage of its assembling with a bank of glass panes including auxiliary terminal flat rigid members. It comprises: posts 301; cross-bars 302; the supporting angles 303; the longitudinal lateral sections 305 of an elongated flexible polymer film; the auxiliary terminal glass panes 304; the glass panes 306; terminal sleeves, which formed by plastic welding the longitudinal lateral sections 305 with sheets 308 of another flexible polymer film.

Figure 3B:
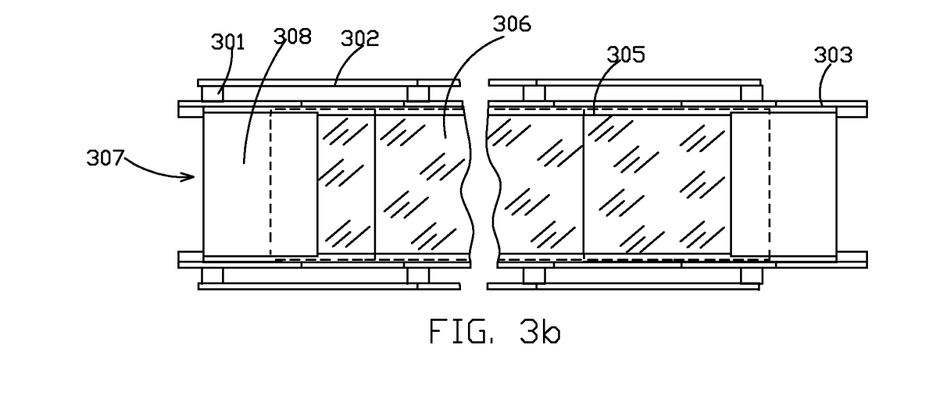
FIG. 3b shows a top view of the shallow closed trough in a preliminary stage of its assembling after removal of the auxiliary terminal flat rigid members.

FIG. 3b shows a top view of the shallow closed trough in a preliminary stage of its assembling after removal of the auxiliary terminal glass panes.

It comprises: posts 301; cross-bars 302; the supporting angles 303; the longitudinal lateral sections 305 of an elongated flexible polymer film; the glass panes 306; the terminal sleeves 307, which are formed by plastic welding the longitudinal lateral sections 305 with sheets 308 of the other flexible polymer film.

Figure 3C:
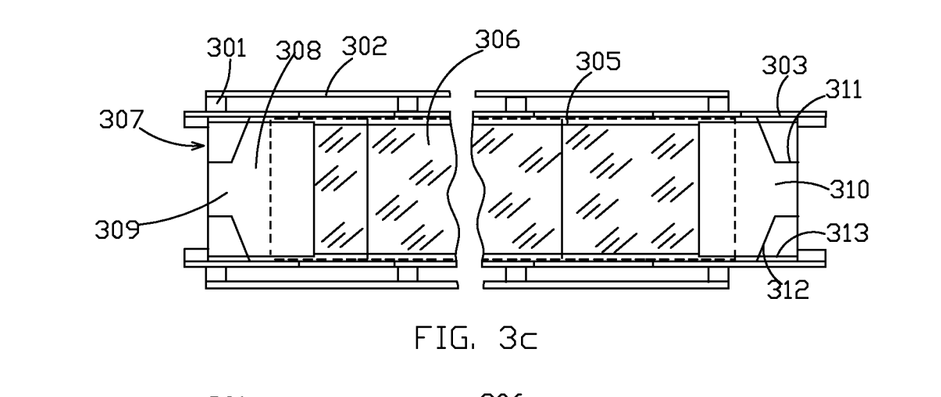
FIG. 3c shows a top view of the shallow closed trough with inlet and outlet ports formed by polymer welding in the terminal sleeves fabricated from the flexible polymer films.

FIG. 3c shows a top view of the shallow closed trough with inlet and outlet ports formed by plastic welding in the abovementioned terminal sleeves.

It comprises: posts 301; cross-bars 302; the supporting angle 303; the longitudinal lateral sections 305 of the elongated flexible polymer film; the glass panes 306; the terminal sleeves 307, which are formed by plastic welding the longitudinal lateral sections 305 with the aforementioned sheets 308; inlet and outlet ports 309 and 310, which are formed by welds 311, 312 and 313.

Figure 3D:
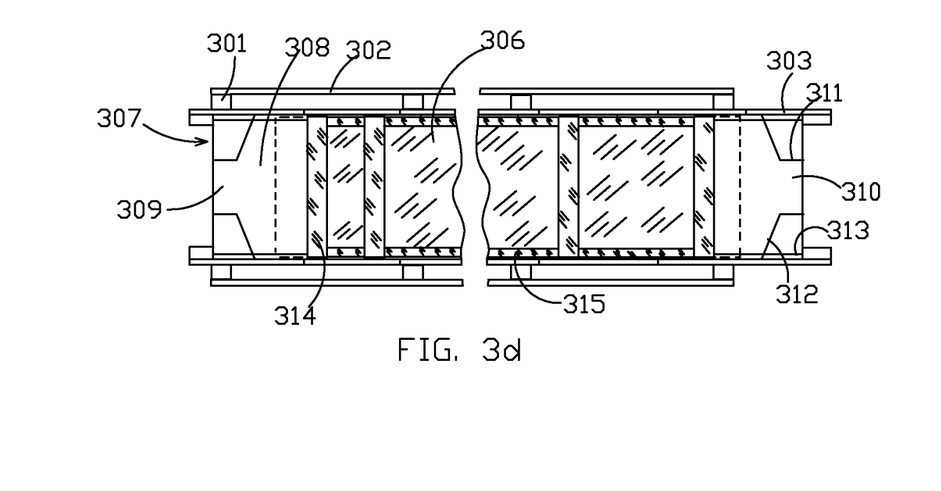
FIG. 3d shows a top view of the shallow closed trough with a bank of glass pane pieces serving for forcing the lateral longitudinal sections of the elongated polymer film against the glass panes, sealing these lateral longitudinal sections and covering the butt joints of the glass panes.

FIG. 3d shows a top view of the shallow closed trough with a bank of glass pane pieces serving for forcing against and sealing the lateral longitudinal sections of the elongated polymer film and covering the butt joints of the glass panes.

It comprises: posts 301; cross-bars 302; the supporting angle 303; the glass panes 306; the terminal sleeves 307, which formed by welding the longitudinal lateral sections 305 with sheets 308 from the other flexible polymer film; glass pane pieces 314 and 315; inlet and outlet ports 309 and 310, which are formed by welds 311, 312 and 313.

Figure 3E:
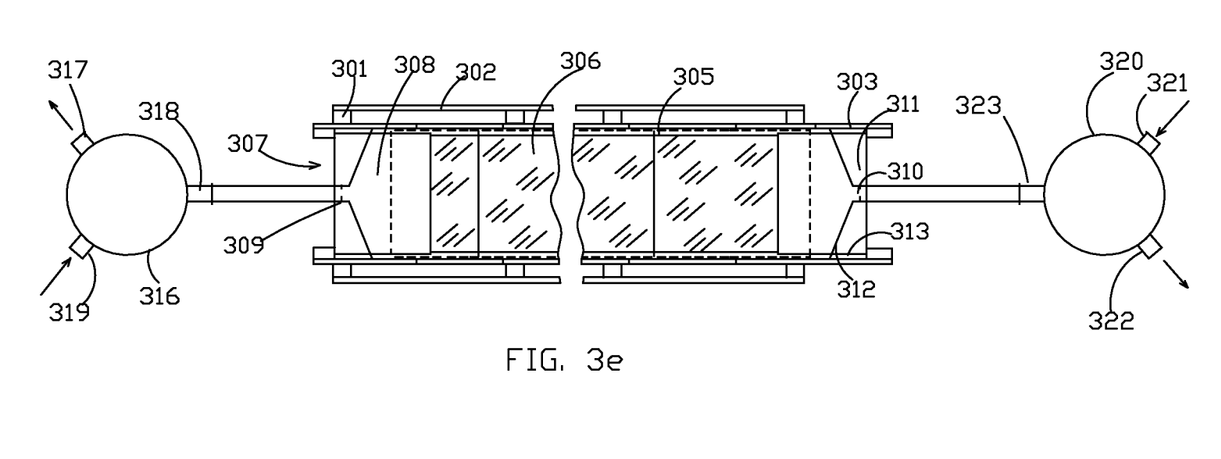
FIG. 3e shows a top view of a photobioreactor comprising the shallow closed trough with the inlet-outlet ports formed by polymer welding in the terminal sleeves fabricated of the flexible polymer films, and two headers, which are in fluid communication with these inlet-outlet ports.

FIG. 3e shows a top view of the photobioreactor comprising the shallow closed trough with the inlet-outlet ports formed by polymer welding in the terminal sleeves fabricated of the flexible polymer films, and two headers, which are in fluid communication with these inlet-outlet ports.

In this case, the photobioreactor operates with counterflow of microalgae suspension and gaseous medium containing $CO_2$.

The photobioreactor comprises: posts 301; cross-bars 302; the supporting angle 303; the longitudinal lateral sections 305 of the elongated flexible polymer film; the glass panes 306; the terminal sleeves 307, which formed by plastic welding the longitudinal lateral sections 305 with sheets 308 of the other flexible polymer film; the inlet and outlet ports 309 and 310, which are formed by welds 311, 312 and 313.

The first header comprises: housing 316; an inlet connection 319 intended for delivery of the microalgae suspension; an outlet connection 317, which serves for withdrawal of the gaseous medium and inlet-outlet connection 318.

The second header comprises: housing 320; an inlet connection 321 intended for delivery of the gaseous medium; an outlet connection 322, which serves for withdrawal of the microalgae suspension and inlet-outlet connection 323.

Figure 4A:
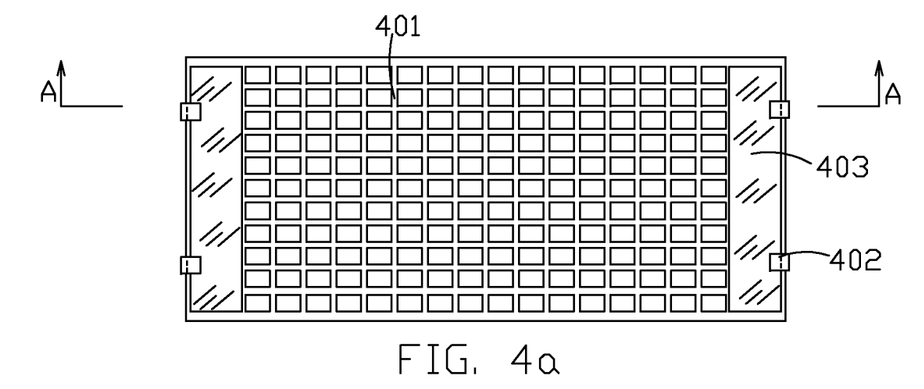
FIG. 4a and FIG. 4b show a top view and a cross-section A-A of a flat rigid member designed as a perforated plate with two clamped glass pane pieces.

FIG. 4a shows a top view of a perforated plate, which fulfils a role of the flat rigid member, with two clamped glass pane pieces. It comprises: the perforated plate 401; attaching clamps 402; glass pane pieces 403.

Figure 4B:
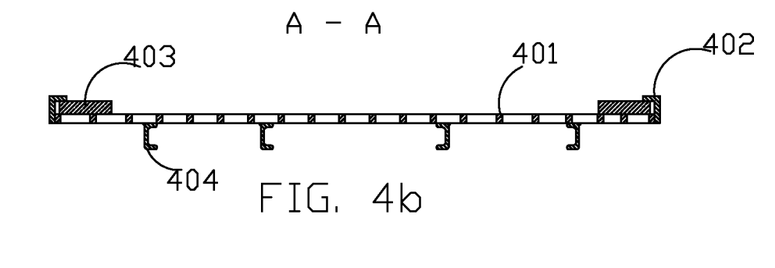

FIG. 4b shows a cross-section A-A of the flat rigid member designed as the perforated plate with two clamped glass pane pieces.

It comprises: the perforated plate 401; the attaching clamps 402; the glass pane pieces 403 with the longitudinal spacers 404.

Figure 5A:
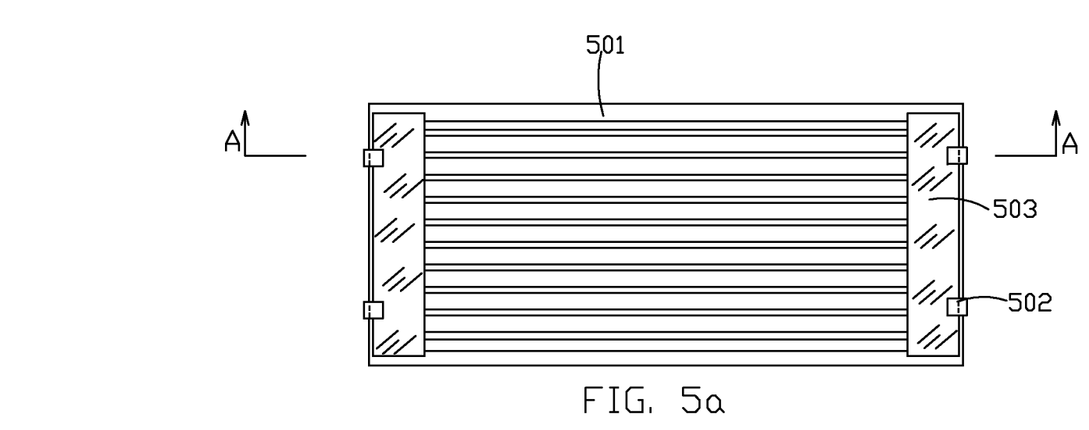
FIG. 5a and FIG. 5b show a top view and a cross-section A-A of a flat rigid member designed as a grate with two clamped glass pane pieces.

FIG. 5a shows a top view and a cross-section A-A of a grate with two clamped glass pane pieces; this grate fulfils a role of the flat rigid member.

It comprises: grate 501; attaching clamps 502 and glass pane pieces 503.

Figure 5B:
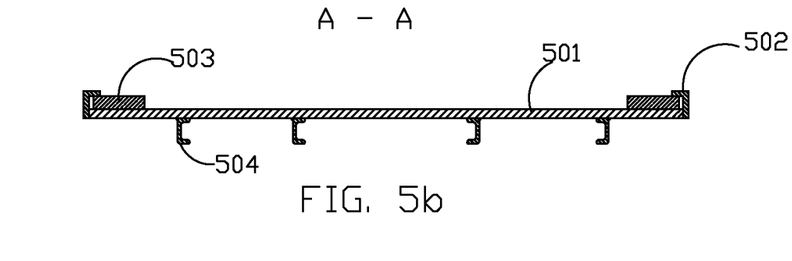

FIG. 5b shows a cross-section A-A of the grate with two clamped glass pane pieces.

It comprises: the perforated plate 501; clamps 502; two glass pane pieces 503 with longitudinal spacers 504.

Figure 6:
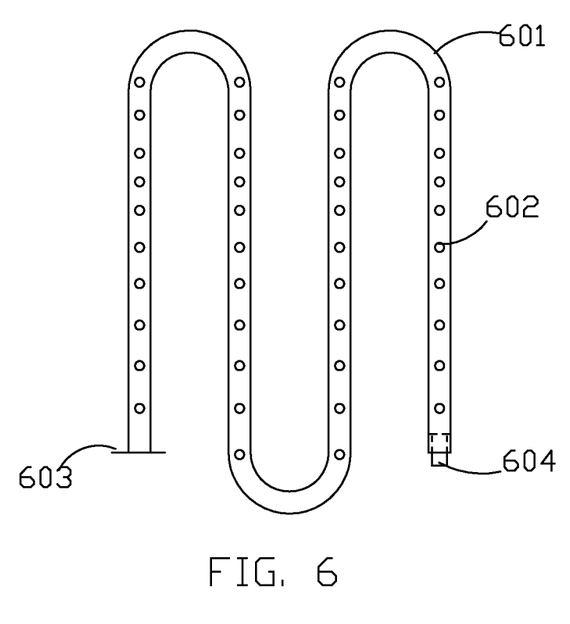
FIG. 6 demonstrates a top view of a flat zigzag pipe to be placed in a transverse channel bar.

FIG. 6 shows a flat zigzag pipe, which is provided with a set of openings; one end of this flat zigzag pipe is plugged and the other end is provided with an inlet connection. It comprises: the flat zigzag pipe 601; openings 602; the inlet connection 603 and plug 604.

The invention claimed is:

1. A photobioreactor for cultivation of microalgae or cyanobacteria comprising: two parallel rows of posts and two parallel rows of inclined supporting angles installed on said posts; said posts with said supporting angles play a role of a supporting unit of said photobioreactor; a shallow closed trough, which fulfils a role of a microalgae or cyanobacteria photo-cultivation chamber; said shallow closed trough is arranged on said supporting unit and said shallow closed trough comprises in turn following parts: an elongated flexible polymer film; the middle longitudinal section of said elongated flexible polymer film fulfils a role of the bottom cover of said shallow closed trough; a bank of translucent flat rigid members and auxiliary terminal flat rigid members, which are abutted in-line with a small inclination to the horizontal plane and placed above said elongated flexible polymer film with supporting by said supporting angles; at least said translucent flat rigid members are provided with longitudinal spacers installed on their undersides; lateral longitudinal sections of said elongated flexible polymer film are bent round edges of said translucent flat rigid members and said auxiliary terminal flat rigid members, and said lateral longitudinal sections of said elongated flexible polymer film are locked with flat longitudinal zones on the upper surfaces of said flat translucent flat rigid members; terminal sections of said shallow closed trough are formed by application of flexible polymer sheets in such a way, that said flexible polymer sheets overlap from above said auxiliary terminal flat rigid members and, additionally, certain sections of said translucent flat rigid members, which are adjacent to said auxiliary terminal flat rigid members; in such a way, said flexible polymer sheets overlap as well areas of said lateral longitudinal sections of said elongated flexible polymer film, which are situated under said flexible polymer sheets; said overlapped areas of lateral longitudinal sections are joined with said flexible polymer sheets by plastic welding with formation of two terminal sleeves of said shallow closed trough; the internal upper edges of said terminal sleeves are sealed with the upper surfaces of said translucent flat rigid members, which are adjacent to said auxiliary terminal flat rigid members; inlet and outlet ports for delivery of a gaseous medium containing $CO_2$ and an aqueous suspension of microalgae or cyanobacteria into the internal space of said shallow closed trough and withdrawal of said gaseous medium and said aqueous suspension of microalgae or cyanobacteria from it; said inlet and outlet ports are formed by plastic welding in said terminal sleeves; two headers, which are established externally to said shallow closed trough; said headers are in fluid communication with said inlet and outlet ports; said first header serves for delivery of said gaseous medium containing $CO_2$ and said aqueous suspension of microalgae or cyanobacteria into said internal space of said shallow closed trough, and said second header serves for withdrawal of said gaseous medium and an aqueous suspension of microalgae or cyanobacteria from the internal space of said shallow closed trough.

2. The photobioreactor for cultivation of microalgae or cyanobacteria as claimed in claim 1, wherein the supporting angles further comprising transverse channel bars joined with the supporting angles on their undersides.

3. The photobioreactor for cultivation of microalgae or cyanobacteria as claimed in claim 1, wherein at least proximal sections (regarding a flow direction of microalgae or cyanobacteria suspension in the shallow closed trough) of the supporting angles are provided with aligning screws in order to minimize misalignment of said proximal section of the shallow closed trough.

4. The photobioreactor for cultivation of microalgae or cyanobacteria as claimed in claim 1, wherein the translucent flat rigid members are transparent glass panes with the longitudinal spacers fastened on their.

5. The photobioreactor for cultivation of microalgae or cyanobacteria as claimed in claim 4, wherein the transparent glass panes are fabricated from UV absorbing glass.

6. The photobioreactor for cultivation of microalgae or cyanobacteria as claimed in claim 1, wherein the translucent flat rigid members are transparent or translucent rigid polymer sheets with the longitudinal spacers fastened on their undersides.

7. The photobioreactor for cultivation of microalgae or cyanobacteria as claimed in claim 6, wherein the both longitudinal lateral sections of the elongated flexible polymer film are joined with the translucent rigid polymer sheet by plastic welding.

8. The photobioreactor for cultivation of microalgae or cyanobacteria as claimed in claim 1, wherein the translucent flat rigid members are rigid perforated sheets with the longitudinal spacers fastened on their undersides.

9. The photobioreactor for cultivation of microalgae or cyanobacteria as claimed in claim 1, wherein the translucent flat rigid members are flat rigid grates with the longitudinal spacers fastened on their undersides.

10. The photobioreactor for cultivation of microalgae or cyanobacteria as claimed in claim 1, wherein said photobioreactor operates with counter flow of the gaseous medium containing $CO_2$ and the microalgae or cyanobacteria suspension.

11. The photobioreactor for cultivation of microalgae or cyanobacteria as claimed in claim 1, wherein said photobioreactor operates with co-current flow of the gaseous medium containing $CO_2$ and the microalgae or cyanobacteria suspension.

12. The photobioreactor for cultivation of microalgae or cyanobacteria as claimed in claim 1, wherein the angles of inclination of the supporting angles are of variable values.

13. The photobioreactor for cultivation of microalgae or cyanobacteria as claimed in claim 1, wherein the elongated flexible polymer film is translucent.

14. The photobioreactor for cultivation of microalgae or cyanobacteria as claimed in claim 1, wherein butt joints between the adjacent translucent flat rigid members and/or the lateral longitudinal sections of said elongated flexible polymer film, which are adjacent to said translucent flat rigid members, are sealed by glue.

15. The photobioreactor for cultivation of microalgae or cyanobacteria as claimed in claim 1, wherein butt joints between the adjacent translucent flat rigid members are sealed by sealing putty in combination with pieces of glass panes overlapping the butt joints and the both longitudinal lateral sections of the flexible polymer film.

16. The photobioreactor for cultivation of microalgae or cyanobacteria as claimed in claim 15, wherein the pieces of the glass panes are forced against the supporting angles by screw clamps.

17. The photobioreactor for cultivation of microalgae or cyanobacteria as claimed in claim 1, wherein butt joints between the adjacent translucent flat rigid members and the both longitudinal lateral sections of the flexible polymer film are sealed by a sealing tape.

18. The photobioreactor for cultivation of microalgae or cyanobacteria as claimed in claim 1, wherein the both longitudinal lateral sections of the elongated flexible polymer film are joined with another elongated flexible polymer film, which overlaps said longitudinal lateral sections, by plastic welding.

19. The photobioreactor for cultivation of microalgae or cyanobacteria as claimed in claim 1, wherein the both longitudinal lateral sections of the elongated flexible polymer film are overlapped and sealingly joined by welding.

20. The photobioreactor for cultivation of microalgae or cyanobacteria as claimed in claim 1, wherein the longitudinal spacers are fabricated from ferromagnetic material and a bank of magnets force from underside the elongated flexible polymer film against the longitudinal spacers of the translucent flat rigid members.

21. The photobioreactor for cultivation of microalgae or cyanobacteria as claimed in claim 1, wherein flow of the gaseous medium containing $CO_2$ in the internal space of the shallow closed trough is executed with variable pressure.

22. The photobioreactor for cultivation of microalgae or cyanobacteria as claimed in claim 1, wherein setting off vibration of the bottom cover of the shallow closed trough is obtained by application of intermittent air jets, which arrive onto the underside of said bottom cover from flat zigzag pipes with sets of openings oriented toward said bottom cover; pressurized air with pulsating pressure is supplied into said flat zigzag pipes.

* * * * *